United States Patent [19]

Linkow et al.

[11] Patent Number: 4,943,236
[45] Date of Patent: Jul. 24, 1990

[54] ASYMMETRICAL BONE DRILL

[75] Inventors: Leonard I. Linkow, New York, N.Y.; Anthony W. Rinaldi, Philadelphia, Pa.; Michael Gambale, West Hanover, Mass.

[73] Assignee: Vent-Plant Corporation, Inc., Philadelphia, Pa.

[21] Appl. No.: 289,853

[22] Filed: Dec. 22, 1988

[51] Int. Cl.⁵ .................................. A61C 3/02
[52] U.S. Cl. ........................ 433/165; 408/59; 408/709
[58] Field of Search ............ 433/165, 124, 104; 128/92 VJ, 305.1, 310; 408/59, 703

[56] References Cited
U.S. PATENT DOCUMENTS
4,842,451 6/1989 Dugger ..................... 408/230

Primary Examiner—Cary E. Stone
Attorney, Agent, or Firm—Darby & Darby

[57] ABSTRACT

A drill for forming a hole in material has a shank with at least a base surface positioned at an angle to a longitudinal axis of the shank and a side surface. A cutting element having first and second ends is eccentrically connected to the base surface in such a manner that a longitudinal axis of the cutting element is situated at a predetermined distance from a longitudinal axis of the shank. An outer surface of the body of the cutting element is defined by at least a front surface and a rear surface intersecting each other along at least a cutting edge. The rear surface is tapered toward the longitudinal axis of the shank so that only the cutting edge and the drill point engage the material and a substantial open area exists between the outer surface of the cutting element and the hole during the entire process of drilling.

16 Claims, 2 Drawing Sheets

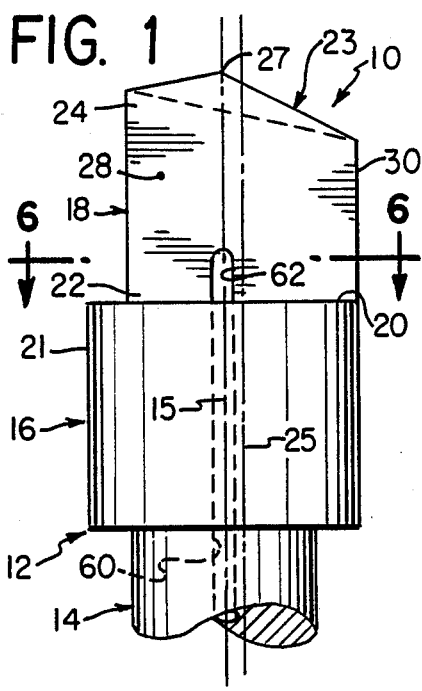
FIG. 1
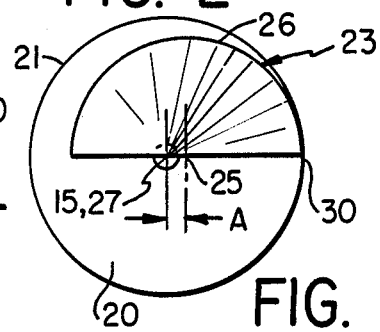
FIG. 2
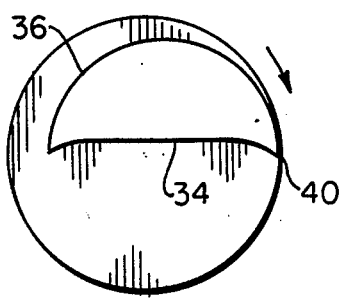
FIG. 3
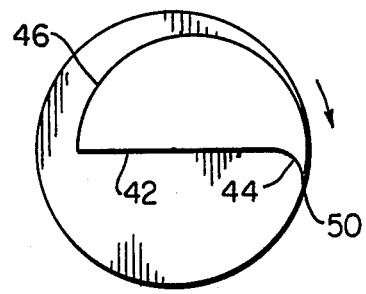
FIG. 4
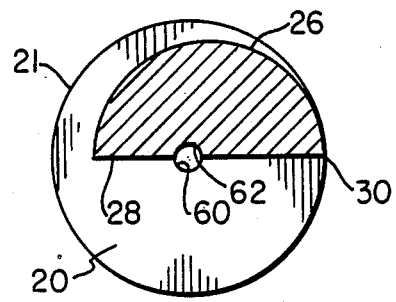
FIG. 5
FIG. 6

ASYMMETRICAL BONE DRILL

BACKGROUND OF THE INVENTION

This invention relates to drilling devices, and more particularly, to asymmetrical drills.

In human and veterinary medicine, it is often necessary to remove or cut live bone, such as in the drilling of holes into teeth in dentistry, the cutting of a jawbone in oral surgery, the cutting of the skull in neurosurgery, etc. In such cases it is highly desirable, and in many cases absolutely necessary, that the surrounding bone not be damaged. This protection of the surrounding bone is particularly necessary to promote the healing of bone about implants inserted in the holes.

Further, damage to such bone can be expected at relatively low temperatures, e.g. teeth or other bony structure will only tolerate temperatures of approximately 50° C. All this makes it important to reduce the amount of heat generated during drilling.

It is known to dissipate frictional heat by conducting cooling fluids, such as water and physiological saline solution, etc., as close as possible to the place of heat formation.

A known type of prior art device dissipates frictional heat by employing nozzles to discharge cooling fluid on the drill bit. In dentistry, these nozzles are usually arranged on a dental handpiece for a drill. The nozzles spray the cooling fluid onto the drilling site. However, this method can not be used when drilling is done in relatively deep holes or if mechanical obstacles prevent the access of the cooling fluid to the tool portion which is in engagement with the substance to be removed.

U.S. Pat. No. 3,762,052 to Melde provides a drill with a longitudinal channel passing through the entire cutting element and which opens outwardly at the working end of the tool. However, the cutting elements of such drills becomes so greatly weakened after hollowing out of the passages that great difficulties of manufacture arise. Moreover, it is technologically difficult and time consuming to make such passages in very compact cutting elements of manufactured from relatively hard material.

In many instances a substantial amount of heat is generated during drilling, as a result of close engagement between a cutting element of a drill and a bone. This often occurs when a symmetrical or concentric cutting member of a drill has a longitudinal axis which is concentric with the longitudinal axis of the drill shank. Such a concentric cutting drill is described by U.S. Pat. No. 4,021,920 to Kirschner et al. During operation of the concentric drill of Kirschner et al, the shank and the cutting element rotate about the same longitudinal axis of rotation. As a result, the opening to be drilled is concentric with the longitudinal axis or the axis of rotation of the cutting element. Therefore, a substantial part of the outside surface of the cutting element engages a significant part of the surface of the bone into which it is drilled. The larger the area of engagement between the bone and the cutting element, the greater the friction and the amount of heat which is generated during the drilling. In the concentric drills such area of engagement and friction is close to the maximum.

When the concentric drill has an irrigation channel which opens at the working end of the drill (see the patent to Melde, for example), the cutting element blocks the irrigation fluid in the hole and prevents the fluid from leaving it. This is because of the substantial engagement between the concentric cutting element and the hole in the bone. As a result, the irrigational fluid blocked in the bone hole can itself reach quite high temperatures and does not effectively reduce the amount of heat generated during the drilling.

Moreover, the symmetrical cutting element, by closing the bone crypt during the process of drilling, prevents the discharge of the cut debris out of the hole or crypt. Thus, in order to facilitate the flushing away of the cut debris, repeated removal of the drill from the crypt and additional irrigation is needed.

SUMMARY OF THE INVENTION

The present invention provides a drill arrangement in which (a) one end of a cutting element is eccentrically connected to a shank in such a manner that the longitudinal axis of the cutting edge is positioned at a distance from the longitudinal axis of the shank, and (b) during operation of the drill arrangement, when the cutting element and shank are rotated, only the cutting element and drill point engage the sides of the hole being drilled and a substantial open area exists between an outside part of the cutting element and the hole during the entire process of drilling.

In an illustrative embodiment of the invention, a drill arrangement includes a shank and a cutting element eccentrically connected to the shank in such a manner that the longitudinal axis of the cutting element is positioned at a predetermined distance from the longitudinal axis of the shank. The free end of the cutting element has a drill point, as well as a rear surface and a front surface which intersect each other along a longitudinal cutting edge. During operation of the drill arrangement, when the shank and cutting element are rotated, only the cutting edge and the drill point engage the surfaces of the hole being drilled. Consequently, the amount of heat created during the process of drilling is substantially diminished since the cutting element is asymmetrically attached to the shank. During rotation of the drill in the bone crypt, only a part of the cross-section of the crypt is covered by the cutting element. The rest of the cross-sectional area is constantly open. As a result, cut debris from the bone is discharged through the opening between the bone and the rotating cutting element. This open area also substantially improves circulation of irrigational fluid within the bone crypt and therefore, enhances the process of dissipation of frictional heat.

In a preferred embodiment of the invention, the shank has a substantially circular cross section. The rear surface of the cutting element body has an arc-shaped configuration and the front surface has a substantially flat configuration so that the cutter has a generally half-circular cross section. The body of the cutting element and the shank are uniform in cross section over the longitudinal axis thereof.

In another embodiment of the invention an internal longitudinal passage extends from an outer end of the shank through the entire body thereof and opens at the cutting element for conducting a cooling medium.

In a still further embodiment of the invention the passage defines a groove within a part of the front surface adjacent the shank in such a manner that the groove is semi-open to on the front surface. A longitudinal axis of the groove is positioned at a distance from the longitudinal axis of the cutting member.

BRIEF DESCRIPTION OF THE DRAWINGS

Other advantages and features of the invention are described with reference to exemplary embodiments, which are intended to explain and not to limit the invention, and are illustrated in the drawings in which:

FIG. 1 is a side view of a drill according to the present invention.

FIG. 2 is an end view of the drill shown in FIG. 1.

FIG. 3 is an end view of another embodiment of the invention.

FIG. 4 is an end view of a further embodiment of the invention.

FIG. 5 is an end view of still another embodiment of the invention.

FIG. 6 is a partial cross-sectional view along line A—A of FIG. 1.

DESCRIPTION OF ILLUSTRATIVE EMBODIMENT

Figure 7:
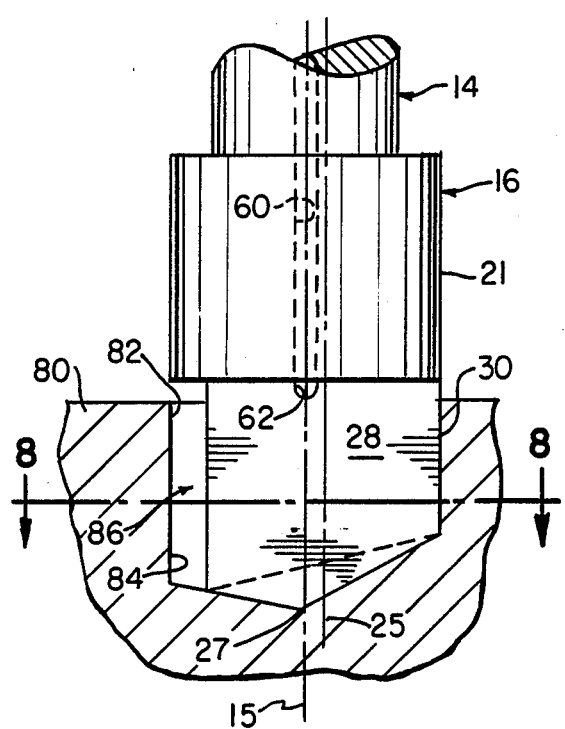
FIG. 7 shows the drill positioned within the hole being drilled during the process of drilling.

Although a specific embodiment of the invention will now be described with reference to the drawings, it should be understood that the embodiment shown is by way of example only and merely illustrative of but one of the many possible specific embodiments which can represent applications of the principles of the invention. Various changes and modifications, obvious to one skilled in the art to which the invention pertains, are deemed to be within the spirit, scope and contemplation of the invention as further defined in the appended claims.

The main parts of a drill 10 shown in FIGS. 1 and 2 are: a shank 12 and a cutting element 18. The shank has a connection part 14 and a base part 16.

The connection part 14 of the shank connects the drill with a rotating device, e.g. a conventional dental handpiece. The base part 16 which is interposed between the connection part and the cutting element is provided with at least a base surface 20 and a side surface 21. The cutting element 18 has a body 23 which extends outwardly from the base surface 20 and is provided with a first end 22 and a second end 24. The first end 22 is eccentrically connected to the base surface 20 and the second end is free. A drill point 27 is located at the second end 24. At the second end 24 a rear surface of the the cutting element is tapered toward the longitudinal axis of the shank. This causes the shape of the drill point shown in FIG. 1 to be asymmetrical. However, it can be made to appear more symmetrical by a change in the angle of taper on one side of the longitudinal axis so that the point edges intersect the sides of the cutting element at the same distance from the surface 20.

In the embodiment of FIGS. 1 and 2 the shank 12 is generally symmetrical about its longitudinal axis 15 and the cutting element 18 which is generally half circular in cross section and asymmetrical about its longitudinal axis 25.

FIG. 1 shows the base surface 20 being substantially perpendicular to the longitudinal axis 15 of the shank. However, angles of inclination between the base surface and the longitudinal axis 15, other than 90°, are permissible.

FIG. 2, which is an end view of the drill 10, illustrates that the cutting element 18 is positioned eccentrically on the base surface 20, i.e. the longitudinal axis of the shank 12 is located at a predetermined distance A from the longitudinal axis 25 of the cutting element 18. However, the drill point 27 is concentric with the longitudinal axis 15 of the shank.

The periphery of the cutting element 18 is defined by a front surface 28 and a rear surface 26 which intersect each other. In the embodiment of FIGS. 1 and 2 the front surface 28 has a substantially flat configuration which is substantially perpendicular to the base surface 20. The rear surface 26 has an arc-shaped configuration. A cutting edge 30 is defined along one line of intersection between the front and rear surfaces.

In the embodiment of FIGS. 1 and 2 the cutting edge 30 is shown as being flush with the side surface 21 of the base part 16. However, other alternatives are possible. For example, FIG. 3 illustrates that the cutting element 18' is shifted toward a central part of the base surface in such a manner that a substantial distance B separates the cutting edge 30' from the side surface 21' of the base.

In the embodiment of FIG. 4 the front surface 34 of the cutting element has a concave configuration. The cutting edge 40 is defined at one line of intersection between the concaved front surface 34 and the arc-shaped rear surface 36.

A front surface 42 of the cutting element shown in FIG. 5 is generally flat, similar to the embodiments of FIGS. 2 and 3. However, a curved portion 44 is provided at one end of the substantially flat front surface. The cutting edge 50 is defined at a place of intersection between the rear surface 46 and the curved part 44 of the front surface.

The drill of the invention may be provided with an irrigation passage 60 for bringing cooling fluid to the hole being drilled. In the embodiment of FIG. 1, it is shown that the passage extend through the entire shank 12 along the longitudinal axis thereof. A part 62 of the passage 60 penetrates into the cutting element 18 and defines a semi-open groove 62 within front surface 28 in the vicinity of the base surface 20. The passage 60 including its part 62 is concentric with the longitudinal axis 15 of the shank.

The length of the semi-open groove 62 within the cutting member may vary. FIG. 1 illustrates the groove 62 extending through about one-fourth of the length of the cutting element. In the embodiment of FIG. 7 only a very short groove extends within the cutting element.

Figure 9:
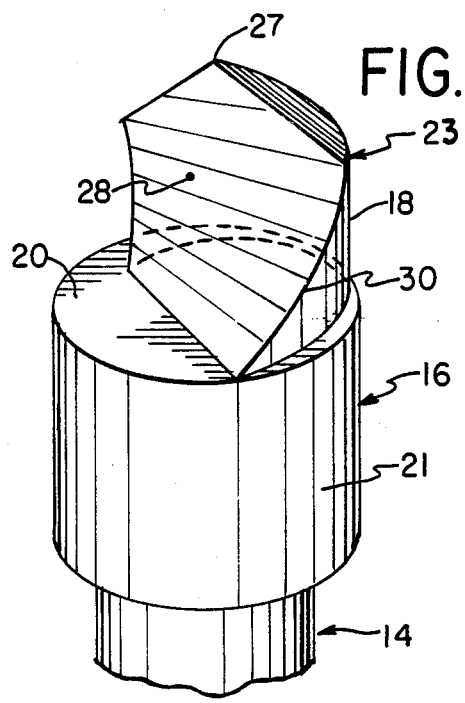
FIG. 9 shows another embodiment of the cutting element in which it is helically twisted.

FIG. 9 illustrates an embodiment of the invention in which the rear surface of the cutting element 18 is made with a spiral twist so that it is somewhat like a conventional drill bit.

Figure 8:
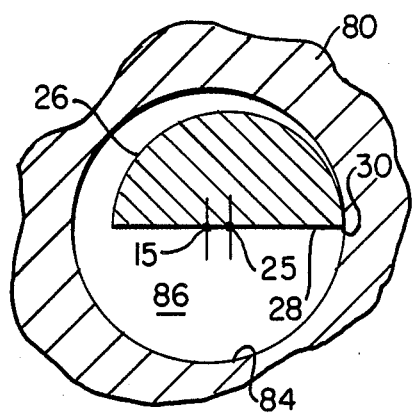
FIG. 8 is a cross-sectional view along line B—B of FIG. 7.

Operation of the drill arrangement is illustrated in FIGS. 7 and 8. If the drill of the invention is used in human or veterinary surgery, an incision is made in the tissue down to the underlying bone 80. The tissue is then reflected and the bone is prepared for drilling. If the drill is used in dentistry, no special preparation for drilling is needed.

The drill 10 is rotated about the longitudinal axis 15 of the shank. The cutting element 18, which is eccentrically attached to the base surface, does not rotate about its longitudinal axis 25, but rotates about the longitudinal axis 15 the shank 12. As a result, a drilled opening 82 is developed which is symmetrical about the longitudinal 15 axis of the shank. In other words, the diameter of the drilled opening 82 is substantially greater than the width of the front surface 28 of the cutting element. FIGS. 7 and 8 show that a substantial open space 86 exists between an outside part of the cutting element 18 and an inside surface 84 of the drilled hole or crypt. It is also illustrated that during the process of drilling, only the cutting edge 30 and the drill point 27 of the cutting element engage the bone.

Since a very limited part of the cutting element contacts the bone during drilling, the friction between the drill and the bone is substantially reduced. The less friction that exists between the drill and the bone, the less heat that is generated at the time of drilling. Because of the rotation of the cutting element within the hole 82, the location of the open space 86 relative to the axis of rotation constantly changes. However, it exists during the entire process of drilling. Since the drill usually rotates at a very high speed, centrifugal forces which developed during the rotation of the cutting element are transferred to cut debris resulting from the drilling of the bone and accumulated within the opening 82. These centrifugal forces cause the cut debris to be rotated within the hole 82 at the speed of rotation of the drill and discharged from the hole 82 through the open space 86.

If a drill having the irrigation passage 60,62 is used (see FIG. 7), the fluid injected into the passage is delivered to a part of the front surface 28 adjacent the base surface 20. The forces of gravity and/or the centrifugal forces developed during the rotation distribute the fluid throughout the hole 82. Because of the constantly moving open space 86, the fluid is not blocked within the hole 82, but instead is constantly discharged from the hole through the open space. Thus, the irrigation fluid efficiently cools the interior of the drilled opening. Furthermore, the fluid flushes away the cut debris from the lower part of the opening and discharges it out of the opening through the open space 86. This discharge of fluid and debris is particularly effective with a bit having a helically twisted cutter part as shown in FIG. 9. This twist tends to lift the debris and fluid out of the hole during rotation of the drill.

What is claimed is:

1. A drill for forming a hole in material comprising:
   a shank having a longitudinal axis;
   a cutting element having a body with a longitudinal center axis extending between first and second ends, said first end of the cutting element being eccentrically connected to said shank in such a manner that the longitudinal axis of the cutting element is positioned at a predetermined distance from the longitudinal axis of the shank, a drill point being located at said second end of the body, said drill point being concentric with the longitudinal axis of the shank, an outer surface of the body of said cutting element being defined by at least a front surface and a rear surface intersecting each other along at least a cutting edge, the rear surface being tapered toward the longitudinal axis of said shank such that during rotation of said shank in the material to form the hole, only the cutting edge and said drill point engage the material and a substantial open area exists between the outer surface of the cutting element and the hole.

2. A drill according to claim 1 wherein said shank has a base part having a base surface with a substantially circular configuration and a side surface, said base surface being substantially perpendicular to the longitudinal axis of the shank.

3. A drill according to claim 2 wherein said rear surface has an arc-shaped configuration and said front surface has a substantially flat configuration, said front surface extending substantially perpendicular to the base surface.

4. A drill according to claim 3 wherein the cutting edge of the cutting element is flush with the side surface of the base part.

5. A drill according to claim 3 wherein the cutting edge of the cutting element is positioned at a distance from the side surface of the base part.

6. A drill according to claim 3 wherein the front surface has a curved extension at one end thereof and the cutting edge is defined along the line of intersection between the curved extension and rear surface.

7. A drill according to claim 2 wherein the front surface, in cross-section, has a concave configuration and said rear surface has an arc-shaped configuration, the cutting edge being defined along a line of intersection between the rear arc-shaped surface and the front concaved surface.

8. A drill according to claim 1 wherein said shank has a base part having a base surface and an outer end situated opposite the base surface, and an internal longitudinal passage extending from the outer end of the shank through the entire body thereof for conducting a cooling medium.

9. A drill according to claim 8 wherein said passage penetrates at least partially into the body of the cutting element.

10. A drill according to claim 9 wherein said passage defines a groove within a part of the body of the cutting element adjacent said base surface in such a manner that said groove is semi-open within the surface.

11. A drill according to claim 9 wherein said passage defines a groove within a part of the cutting element and said groove is positioned within the body of the cutting element.

12. A drill according to claim 11 wherein a longitudinal axis of the groove is concentric with the longitudinal axis of the shank.

13. A drill according to claim 1 wherein said shank has a connection part for connection with a rotary device and a base part connected to the cutting element, said base part including side surfaces and a base surface positioned at an angle to the longitudinal axis of the shank.

14. A drill according to claim 1 wherein the hole to be drilled is symmetrical relative to the longitudinal axis of the shank and is asymmetrical to the longitudinal axis of the cutting element.

15. A drill according to claim 1 wherein said substantial open area exists between the outer surface of the cutting element and the hole during the entire process of drilling.

16. A drill according to claim 1 wherein said cutting element has a spiral twist.

* * * * *